US012727816B2

(12) United States Patent
Pan et al.

(10) Patent No.: US 12,727,816 B2
(45) Date of Patent: Sep. 8, 2026

(54) SYSTEM AND METHOD FOR VIBRATION-BASED MEDICATION INTERACTION RECOGNITION

(71) Applicant: The Regents of the University of California, Oakland, CA (US)

(72) Inventors: Shijia Pan, Merced, CA (US); Yue Zhang, Merced, CA (US); Dong Yoon Lee, Merced, CA (US); Yihong Li, Merced, CA (US); Alyssa M. Weakley, Sacramento, CA (US); Hao-Chuan Wang, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 98 days.

(21) Appl. No.: 18/941,135

(22) Filed: Nov. 8, 2024

(65) Prior Publication Data

US 2025/0152091 A1 May 15, 2025

Related U.S. Application Data

(60) Provisional application No. 63/598,040, filed on Nov. 10, 2023.

(51) Int. Cl.
*A61B 5/00* (2006.01)
*G16H 20/13* (2018.01)

(52) U.S. Cl.
CPC .......... *A61B 5/4833* (2013.01); *G16H 20/13* (2018.01)

(58) Field of Classification Search
CPC ....... A61B 5/4833; G16H 20/10; G16H 20/13
See application file for complete search history.

(56) References Cited

U.S. PATENT DOCUMENTS

2014/0262252 A1* 9/2014 Slepicka .............. E21B 47/095 166/255.2
2018/0008516 A1* 1/2018 Afsarifard ................ A61J 1/03
2021/0247269 A1* 8/2021 Laricchiuta ............ G01H 1/003
2021/0270866 A1* 9/2021 Laurent ................... G01P 1/023
2023/0170068 A1* 6/2023 Shattock ................ G16H 40/63 705/2

OTHER PUBLICATIONS

Geophone • SM-24 • SEN-11744—Spark/fun Electronics. https://wv.rw.sparkfun.com/products/11744.

(Continued)

*Primary Examiner* — Omer S Khan
(74) *Attorney, Agent, or Firm* — Carter, DeLuca & Farrell LLP

(57) ABSTRACT

A system and method for monitoring medication intake uses vibration signals generated by a kinetic augmentation attachment. The attachment includes a base coupled to a medication container, a spring, and a weight, which produces distinct vibration signatures when the container is placed on a surface. A vibration sensor detects these signals, and a computing device processes them to extract features of the attachment and identify the medication container. The system does not require batteries, enabling long-term, maintenance-free monitoring. The method includes processing vibration signals using frequency analysis and machine learning to recognize different medication containers based on their kinetic signatures.

20 Claims, 7 Drawing Sheets

(56) References Cited

OTHER PUBLICATIONS

Murtadha Aldeer, Musaab Alaziz, Jorge Ortiz, Richard E Howard, am! Richard P Marlin. 2019. A sensing-based framework for medication compliance monitoring. In Proceedings of the 1st ACM International Workshop on Device-Free Human Sensing. 52-56.
Murtadha Aldecr, Mehdi Javanmard, and Richard P Martin. 2018. A review of medication adherence monitoring technologies. Applied System Innovation 1, 2 (2018). 14.
RODR Carlos. 2020. IoT-based smart medicine dispenser to control and supervise medication intake. In Intelligent Environments 2020: Workshop Proceedings of the 16th International Conference on Intelligent Environments, vol. 28. IOS Press, 39.
M. Robin DiMatteo, Patrick J Giordani, Heidi S Lepper, and Thomas W Croghan. 2002. Patient adherence and medical treatment outcomes a meta-analysis. Medical care (2002), 794-811.
Slah Drira. Sai GS Pai, Yves Reuland Nils FH Olsen. and Ian FC Smith. 2021. Using footstep-induced vibrations for occupant detection and recognition in buildings. Advanced Engineering Informatics 49 (2021), 101289.
Zhizhang Hu. Emre Sezgin, Simon I.in, Pei Zhang, Hae Young Noh, and Shijia Pan. 2019. Device-free sleep stage recognition through bed frame vibration sensing. In Proceedings of the 1st ACM International Workshop on Device-Free Human Sensing. 39-43.
Robert L Jackson, Itzhak Green, and Dan B Marghitu. 2010. Predicting the coefficient of restitution of impacting elastic- perfectly plastic spheres. Nonlinear Dynamics 60 (2010). 217-229.
Beena Jimmy and Jimmy Jose. 2011. Patient medication adherence: measures in daily practice. Oman medical journal 26. 3 (2011), 155.
Haik Kalantarian, Nabil Alshurafa, Ebrahim Nemati, Tuan Le, and Majid Sarrafzadeh. 2015. A smartwatch-based medication adherence system. In 2015 IEEE 12th International Conference on Wearable and Implantable Body Sensor Networks (USN). IEEE. 1-6.
Haik Kalantarian. Babak Motamed. Nabil Alshurafa, and Majid Sarrafzadeh. 2016. A wearable sensor system for medication adherence prediction. Artificial intelligence in medicine 69 (2016), 43-52.
Kathryn P Lowry, Tara K Dudley. Eugene Z Oddone. and Hayden B Bosworth. 2005. Intentional and unintentional nonadherence to antihypertensive medication. Annals of Pharmacotherapy 39. 7-8 (2005) 1198-1203.
Corey McCall, Branden Maynes. Cliff Zou, and NingJ Zhang. 2010. RMAIS: RFID-based medication adherence intelligence system. In 2010 Annual International Conference of the IEEE Engineering In Medicine and Biology. IEEE, 3768-3771.
PK Nijiya Jabin Najeeb, Aysha Rimna, KP Safa, M Silvana, and TK Adarsh. 2018. Pill care-the smart pill box with remind, authenticate and confirmation function. In 2018 International Conference on Emerging Trends and Innovations In Engineering And Technological Research (ICETIETR). IEEE. 1-5.
Juergen Morak. Mark Schwarz, Dieter Hayn. and Guenter Schreier. 2012. Feasibility of mHealth and Near Field Communication technology based medication adherence monitoring. In 2012 Annual Inte•• national Conference of the IEEE Engineering in Medicine and Biology Society. IEEE. 272-275.
Rafael Mrosek, Tobias Dehling, and Ali Sunyaev 2015. Taxonomy of health IT and medication adherence. Health Policy and Technology 4, 3 (2015), 215-224.
Shijia Pan, Mario Berges, Juleen Rodakowski, Pei Zhang, and Hae Young Noh.2019. Fine-grained recognition of activities of daily living through structural vibration and electrical sensing. In Proceedings of the 6th ACM International Conference on Systems for Energy-Efficient Buildings. Cities, and Transportation. 149-158.
Gerard Reach. 2005. Role of habit in adherence to medical treatment. Diabetic Medicine 22. 4 (2005). 415-420.
Joshua Ernest Pedi Reddy and Ameet Chavan. 2020. AI-IoT based smart pill expert system. In 2020 4th International Conference Trends in Electronics and Informatics (ICOEI) (48184). IEEE, 407-414.
AS Sadun, J Jalani, and JA Sukor. 2016. Force Sensing Resistor (FSR): a brief overview and the low-cost sensor for active compliance control. In First international workshop on pattern recognition. vol. 1001 I. SPIE, 2.!2-226.
T.L. Skaer, DA Sclar. DJ Markowski, and JK Won. 1993. Effect of value-added utilities on prescription refill compliance and health care expenditures for hypertension. Journal of human hypertension 7, 5 (1993), 515-518.
Brenda C Spillman. Eva H Allen. and Melissa Favreault. 2021. Informal caregiver supply and demographic changes: Review of the literature. Office of the Assistant Secretary for Planning and Evaluation Report (2021).
Thulasi Thiruchselvam. Gary Naglie, Rahim Moineddin, Jocelyn Charles. Laura Orlando. Susan Jaglal, William Snow, and Mary C Tierney. 2012. Risk factors for medication nonadherence in older adults with cognitive impairment who live alone. International journal of geriatric psychiatry 27. 12 (2012), 1275-1282.
Shirley S Travis, Lisa Sparks Bethea, and Peter Winn. 2000. Medication administration hassles reported by family caregivers of dependent elderly persons. The Journals of Gerontology Series A: Biological Sciences and Medical Sciences 55, 7 (2000), .M412-M417.
James F Tressler. Sedat Alkoy, and Robert E Newnham. 1998. Piezoelectric sensors and sensor materials. Journal of electroceramics 2 (1998), 257-272.
Liangqi Yuan. Hongwei Qu, and Jia Li. 2021. Velostat sensor array for object recognition. IEEE Sensors Journal 22, 2 (2021), 1692-1704.
Yue Zhang, Shiwei Fang, Carlos Ruiz, Zhizhang Hu, Shubham Rohal, and Shijia Pan. 2023. Augmenting Vibration-Based Customer-Product Interaction Recognition with Sparse Load Sensing. In Proceedings of Cyber-Physical Systems and Internet of Things Week 2023. 266-271.
Yang Zhang, Gicrad Laput. and Chris Harrison. 2018. Vibrosight: Lon•• range vibrometry for smart environment sensing. In Proceedings of the 31st Annual ACM Symposium on User Interface Software and Technology. 225-236.
Diaa Salama Abdul Minaam and Mohamed Abd-ELfattah. 2018. Smart drugs: Improving healthcare using smart pill box for medicine reminder and monitoring system. Future Computing and Informatics Journal 3, 2 (2018), 443-456.
Jonathon Fagert, Mostafa Mirshekari, Shijia Pan, Linda Lowes, Megan lammarino, Pei Zhang, and Hae Young Noh. 2021. Structure- and sampling-adaptive gait balance symmetry estimation using footstep-induced structural floor vibrations. Journal of Engineering Mechanics 147, 2 (2021), 04020151.
Yue Zhang, Carlos Ruiz, Shubham Rohal, and Shijia Pan. 2023. CPA: Cyber-Physical Augmentation for Vibration Sensing in Autonomous Retails. In Proceedings of the 24th International Workshop on Mobile Computing Systems and Applications. 8-14.

* cited by examiner

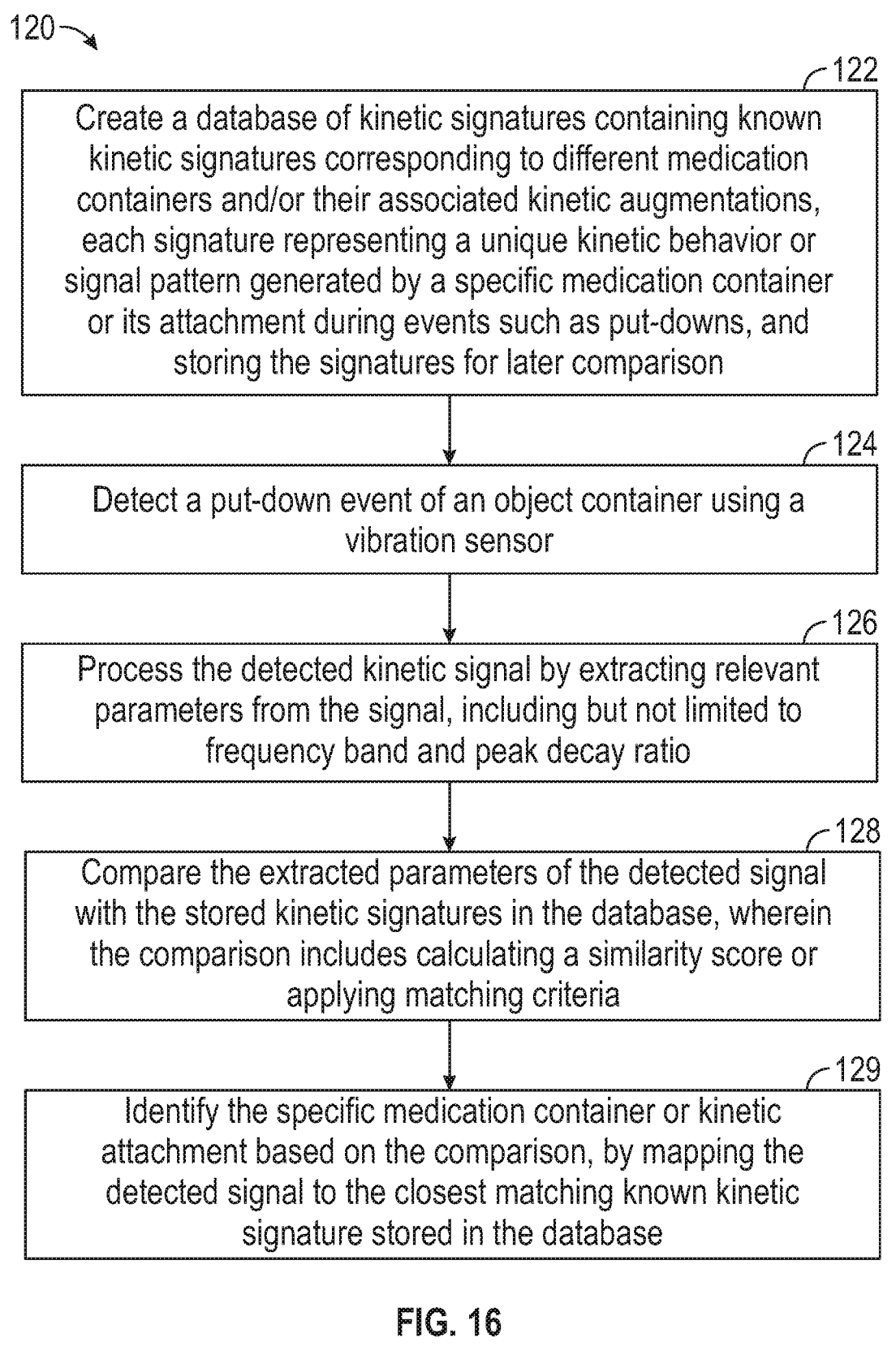

120

122 Create a database of kinetic signatures containing known kinetic signatures corresponding to different medication containers and/or their associated kinetic augmentations, each signature representing a unique kinetic behavior or signal pattern generated by a specific medication container or its attachment during events such as put-downs, and storing the signatures for later comparison 124 Detect a put-down event of an object container using a vibration sensor 126 Process the detected kinetic signal by extracting relevant parameters from the signal, including but not limited to frequency band and peak decay ratio 128 Compare the extracted parameters of the detected signal with the stored kinetic signatures in the database, wherein the comparison includes calculating a similarity score or applying matching criteria 129 Identify the specific medication container or kinetic attachment based on the comparison, by mapping the detected signal to the closest matching known kinetic signature stored in the database

FIG. 16

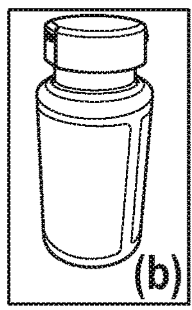
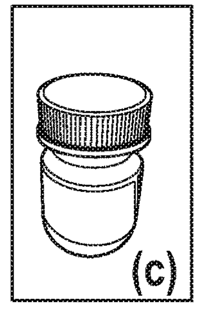
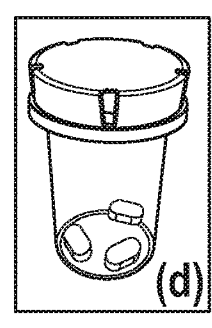
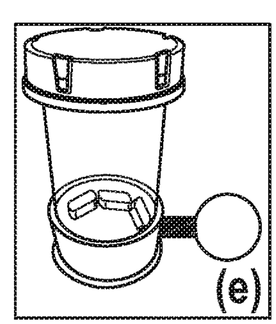
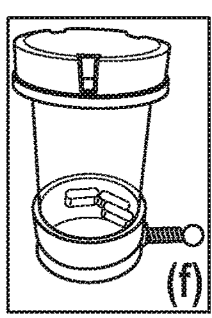
FIG. 17
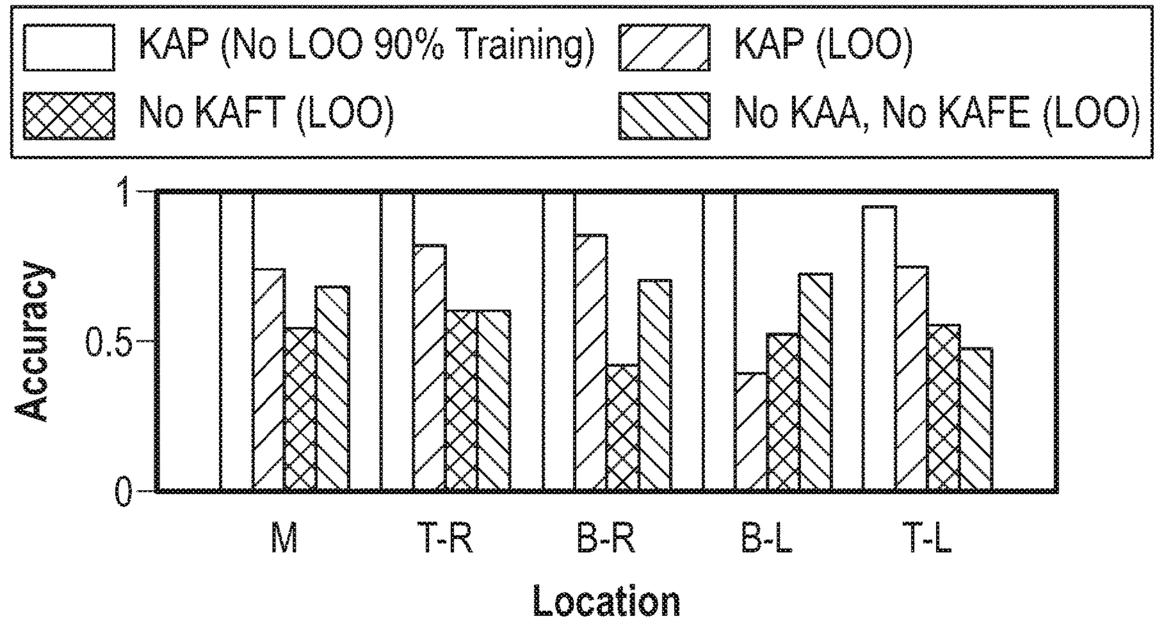
FIG. 18

SYSTEM AND METHOD FOR VIBRATION-BASED MEDICATION INTERACTION RECOGNITION

CROSS-REFERENCE TO RELATED APPLICATION

The present application claims the benefit of and priority to U.S. Provisional Patent Application Ser. No. 63/598,040, filed on Nov. 10, 2023. The entire contents of the foregoing application are incorporated by reference herein.

BACKGROUND

Physicians frequently prescribe medications as a common tool to manage symptoms and diseases. However, patients vary widely in how strictly they follow their prescribed treatments. Medication adherence, which often relies on self-reported assessments, is an uncontrolled variable in modern medicine. This presents challenges not only for the patients but also for physicians and caregivers. This issue is particularly concerning for older adults with cognitive impairment. For example, a study of elderly individuals taking at least one medication found a 17.4% rate of non-adherence. In countries like the U.S., where caregivers are in short supply, the burden on caregivers to ensure medication adherence is increasing. Physicians also face difficulties managing patients' medication plans and determining the causes of medical emergencies, often due to potential non-adherence.

The problem of medication non-adherence is primarily due to unintentional rather than deliberate noncompliance. Forgetfulness is a major factor, with nearly half of patients reporting it as the reason for deviating from their prescription plans. To address the lack of monitoring for medication intake, various Internet of Things (IoT) systems have been developed. Customized on-container sensing systems, although effective, often face battery-related issues and require frequent maintenance. Vision-based medication dispensers necessitate initial installation and regular refills. Additionally, RFID- and NFC-based sensing approaches typically require a designated platform or reader with specific usage protocols. As a result, there is a need for a battery-free and non-intrusive system that allows continued use of the standard medication container while enabling effective medication interaction monitoring.

SUMMARY

According to one embodiment of the present disclosure, a system for monitoring medication intake based on interaction with a medication container is disclosed. The system includes a kinetic augmentation attachment configured to be coupled to the medication container. The attachment includes a base for coupling to the medication container; a spring coupled to the base at a first end; and a weight coupled to a second end of the spring, where the kinetic augmentation attachment generates a vibration signal when the medication container is placed on a surface. The system also includes one or more vibration sensors configured to detect the vibration signal generated by the placement of the medication container on the surface. The system also includes a computing device in communication with the vibration sensor. The computing device is configured to receive the vibration signal from the vibration sensor, process the vibration signal to extract features indicative of the kinetic augmentation attachment, and identify the medication container coupled to the kinetic augmentation attachment based on the extracted features.

Implementations of the above embodiment may include one or more of the following features. According to one aspect of the above embodiment, the weight may be formed from one of metal, rubber, or thermoplastic polymer. The spring may be one of a coil spring, an elastomeric rod, or a leaf spring. The computing device may be also configured to apply a short-time Fourier transform (STFT) to the received vibration signals to generate a spectrogram for analysis. The computing device may be further configured to extract a frequency band from the spectrogram; sum energy across the extracted frequency band; and use a peak detection algorithm to identify points of interest in the signal. The computing device may be additionally configured to access a database storing kinetic signatures corresponding to a plurality of medication containers and corresponding kinetic augmentation attachments. The computing device may be also configured to compare the extracted features of the detected vibration signal to the stored kinetic signatures in the database to match the vibration signal with a specific medication container. The computing device may be also configured to execute a machine learning algorithm to identify the kinetic augmentation attachment based on the extracted features. The machine learning algorithm may be a support vector machine. The vibration sensor may be one of a piezoelectric sensor, accelerometer, or a MEMS vibration sensor.

According to another embodiment of the present disclosure, a method for identifying a medication container is disclosed. The method includes detecting a vibration signal using a vibration sensor, the vibration signal generated by placing a medication container on a surface. The medication container includes a kinetic augmentation attachment having a base for coupling to the medication container, a spring coupled to the base at a first end, and a weight coupled to a second end of the spring, where the kinetic augmentation attachment generates a vibration signal when the medication container is placed on a surface. The method also includes processing the vibration signal to extract signal features indicative of the kinetic augmentation attachment. The method further includes identifying the medication container coupled to the kinetic augmentation attachment based on the detected vibration signals. The method additionally includes outputting the identified medication container to a user.

Implementations of the above embodiment may include one or more of the following features. According to one aspect of the above embodiment, the weight may be formed from one of metal, rubber, or thermoplastic polymer. The spring may be one of a coil spring, an elastomeric rod, or a leaf spring. The method may include applying an STFT to the vibration signals to generate a spectrogram for analysis. The method may also include extracting a frequency band from the spectrogram; summing energy across the extracted frequency band; and identifying points of interest in the signal using a peak detection algorithm. The method may also include accessing a database storing kinetic signatures corresponding to a plurality of medication containers and corresponding kinetic augmentation attachments. The method may also include comparing the extracted signal features of the detected vibration signal to the stored kinetic signatures in the database to match the vibration signal with a specific medication container. The method may also include using a machine learning algorithm to identify the kinetic augmentation attachment based on the extracted signal features. The machine learning algorithm may be a support vector machine. The vibration sensor may be one of a piezoelectric sensor, accelerometer, or a MEMS vibration sensor.

BRIEF DESCRIPTION OF DRAWINGS

Various embodiments of the present disclosure are described herein below with reference to the figures wherein:

FIG. 16 is a flow chart of a method for determining a type of the medication container according to an embodiment of the present disclosure;

FIG. 17 is an image of different medication containers identified using the system of FIG. 2 based on a vibration signal according to an embodiment of the present disclosure; and FIG. 18 shows a bar graph of recognition accuracy for recognizing different medication containers using the system of FIG. 2.

DETAILED DESCRIPTION

The present disclosure provides a system and method for tracking when an item has been put down on a surface by identifying a placement event using a vibration or an acoustic sensor configured to detect and analyze vibration induced by a kinetic augmentation attachment attached to the object. The object may be a medication container or any other item or container to be tracked.

The present disclosure provides a kinetically augmented medication container, which integrates seamlessly with a surface vibration-based sensing system to monitor medication adherence. The system detects surface vibrations induced when medication containers are placed down, enabling the identification and tracking of specific containers. The kinetic augmentation attachment does not require modifications to the medication containers or the underlying vibration-based activity recognition systems. The attachment embeds identity information into the vibration signal generated by the interaction between the user and the medication container during placement. As a result, the system is battery-free, unlike some conventional medication adherence tracking systems, thereby minimizing maintenance requirements.

To achieve robust recognition of different medication containers, the disclosure incorporates a feature extraction algorithm based on kinetic models. The approach involves modifying the physical properties of ambient objects, such as medication containers, to embed unique identity information within their kinetic signatures. By doing so, the system enables accurate recognition and monitoring of interactions with the containers. Moreover, the disclosure includes the design of a kinetically augmented medication container and a corresponding recognition algorithm, specifically intended to address the challenge of unintentional medication non-adherence. To validate the system, real-world testing was conducted using 3D-printed kinetic-augmentation attachments.

Figures 1, 2, 3:
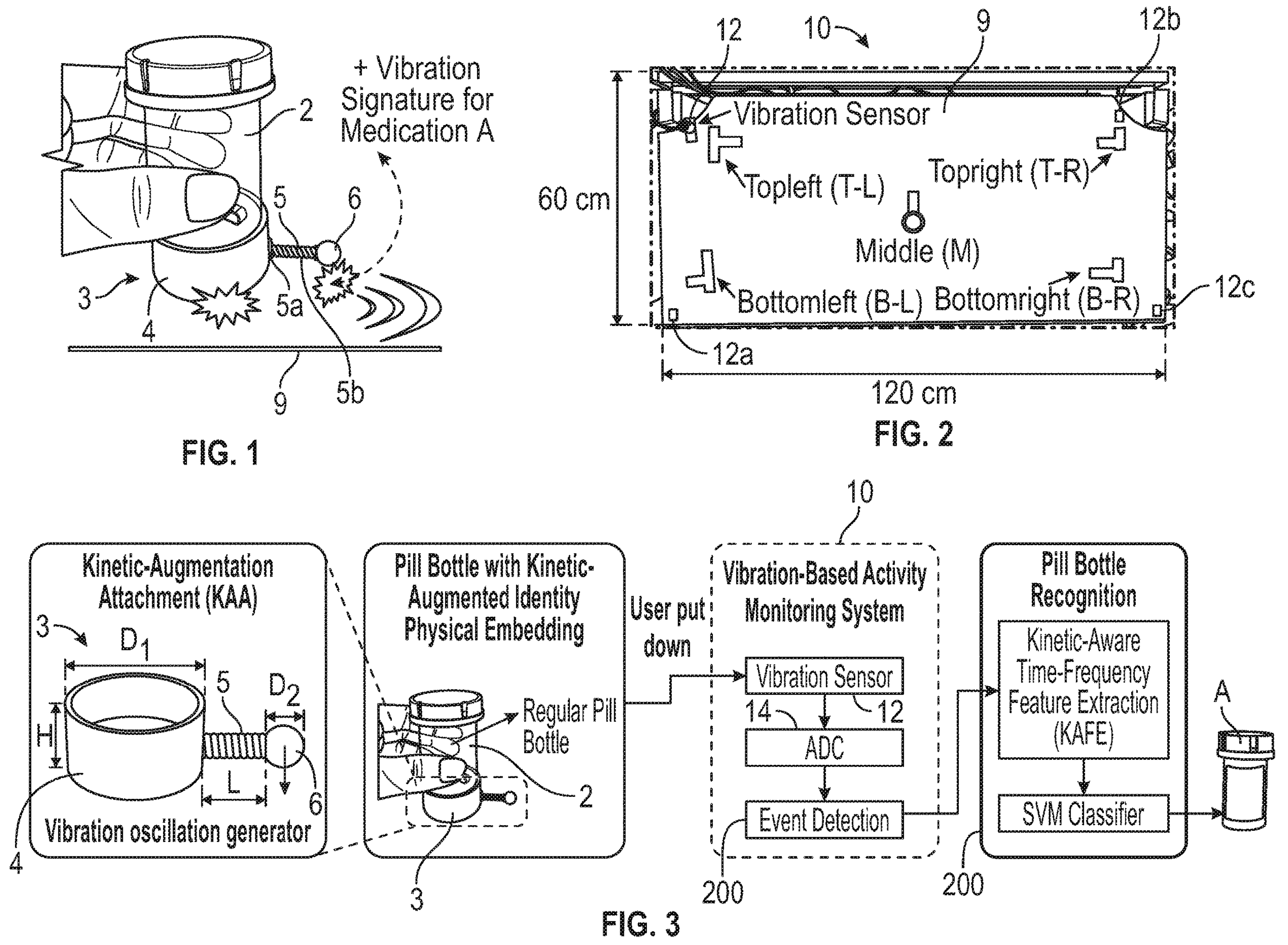
FIG. 1 is a side view of a medication container with a kinetic augmentation attachment according to an embodiment of the present disclosure.
FIG. 2 is an image of a system for detecting vibration generated by the kinetic augmentation attachment according to an embodiment of the present disclosure.
FIG. 3 is a schematic diagram of the system of FIG. 2 for detecting vibration generated by the kinetic augmentation attachment during placement of the medication container according to an embodiment of the present disclosure.

With reference to FIG. 1, an object, such as a medication container 2, is shown, with a kinetic augmented attachment 3 coupled thereto. The attachment 3 includes a base 4 for coupling to the medication container 2, a spring 5 secured to the base 4 at its first end 5*a*, and a weight 6, which is secured to a second end 5*b* of the spring 5. The spring 5 may be a coil spring, an elastomeric rod, a leaf spring, and the like. The weight 6 may be formed from any material, such as metal, thermoplastic polymer, rubber, and may have any desired shape, such as a ball, a polyhedron, or any other desired shape or form. The base 4 may be formed from any material to provide for secure coupling of the attachment to the container 2 and may have a shape that matches at least a portion of the container 2 to allow for frictional engagement of the base 4 with the container 2. In one embodiment, the base 4 may enclose between 1%-15% of the surface of the container 2. In another embodiment, the base 4 may enclose between 5%-50% of the surface of the container 2. The base 4 may be formed from a variety of materials, such as metal, thermoplastic polymers, or rubber, providing flexibility in terms of strength and durability. For example, lightweight plastics or strong metals can be selected based on the specific needs of the attachment. The base 4 can be fabricated using various manufacturing techniques, including but not limited to 3D printing, injection molding, or CNC machining. Each method offers distinct advantages, such as rapid prototyping with 3D printing, high precision with CNC machining, or mass production efficiency with injection molding. As shown in the first two (from the left) panels of FIG. 3, the base 4 has a cylindrical shape to fit around the cylindrical shape of the container 2. However, this is not intended to be limiting as the base 4 may be formed of any desired shape to fit around any type of container, such as a square, triangle, and the like.

The spring 5 can be attached to the base 4 and the weight 6 in various ways, depending on the design requirements and materials used. For example, the spring 5 may be secured to the base 4 and the weight 6 using adhesives such as epoxy or industrial glue, which provide a strong and durable bond. The spring 5 may also be attached by press fitting, where the spring is tightly inserted into corresponding slots or holes in the base 4 and the weight 6, relying on friction to hold it in place. Additionally, welding or soldering may be employed when the components are made of metal, providing a permanent and robust attachment.

When the medication container 2, equipped with the kinetic augmented attachment 3, is put down on a surface 9, the weight 6 impacts the surface 9, and bounces, generating unique vibration signals. The surface 9 may be a medicine cabinet shelf, table, or any other desired surface. These signals reflect the identity signature of the container 2, which can be detected and used for medication intake recognition. A system 10 for detecting placement of the container 2, and in particular, the vibrations of the weight 6, is shown in FIGS. 2 and 3. In one embodiment, the system 10 operates without the need for batteries for each of the attachments 3, making it suitable for long-term, continuous use without maintenance.

In another embodiment the vibration sensor 12 may be integrated directly within the kinetic augmentation attachment 3. By embedding the sensor 12 within the attachment 3, the need to select a specific surface 9 in advance is eliminated, allowing the sensor 12 to accompany the medication container 2 wherever it is placed, enhancing portability and ease of use.

In yet another embodiment, the system 10 may include a mat with embedded vibration sensors 12, where the mat itself is configured to be placed on a surface 9. This mat could incorporate built-in power generation to operate the sensors 12, enabling vibration detection without a permanent surface installation. The mat provides a versatile and adaptable solution, allowing reliable detection of the medication container 2 placement across varied environments and multiple surfaces.

Figure 4:
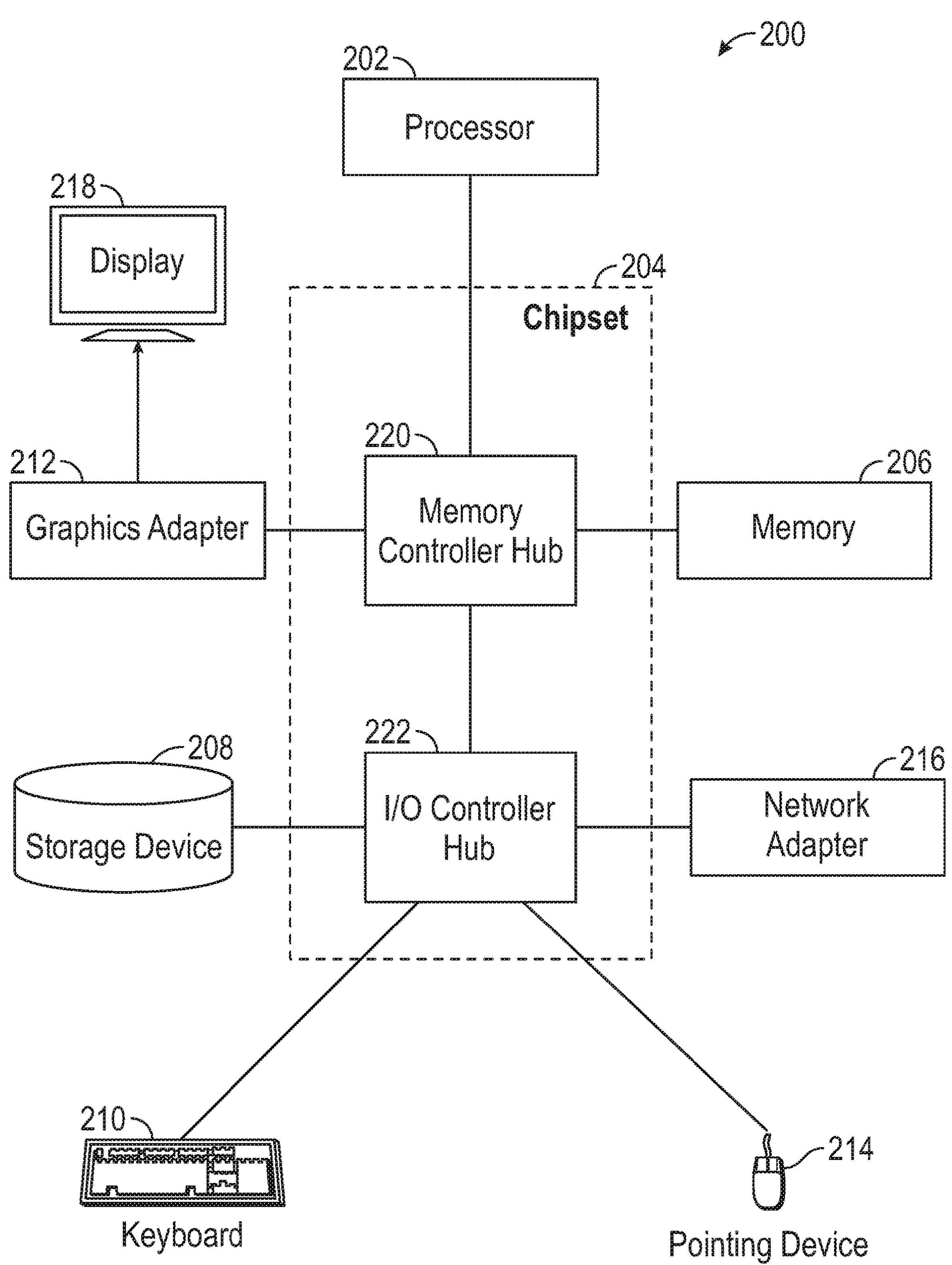
FIG. 4 is a schematic diagram of a processing device for use with the system of FIG. 2 according to an embodiment of the present disclosure.

The kinetic augmentation attachment 3, as shown in FIG. 4, may be manufactured with varying dimensions and materials to optimize its performance for different applications. The base 4 can have a diameter from 20 mm to 60 mm, with a height between 10 mm and 30 mm, depending on the specific requirements for securely coupling the attachment 3 to the medication container 2. For example, the base 4 may have a height to enclose between about 1%-15% the height of the container. In another example, the base 4 may have a height to enclose between about 1%-50% of the height of the container.

The spring 5 used in the attachment 3 can also vary in its properties, such as stiffness, length, and material composition. In certain configurations, the spring 5 may have a length ranging from 5 mm to 30 mm and may be selected from materials like metal or elastomers, depending on the desired oscillatory response.

Additionally, the weight 6 attached to the spring 5 may be configured with varying diameters and materials to affect the resulting vibration signature. For instance, one configuration may utilize a metal ball with a diameter from about 3 mm to about 15 mm, while another configuration may use a rubber ball with a larger diameter from about 20 mm to about 30 mm. These variations in the dimensions and material properties of the weight 6, spring 5, and base 4 allow the attachment 3 to generate distinct vibration patterns, which can be used to effectively differentiate between medication containers 2 based on their kinetic signatures.

The attachment 3 may be modified in a variety of ways to provide for a plurality of unique vibration signatures. Modifiable parameters include various elasticity levels, sizes, and lengths for both the spring 5 and the weight 6. While only two types of weights are disclosed herein with different sizes and materials, further configuration combinations are envisioned, allowing the attachment 3 to be fine-tuned for a wider range of options.

With reference to FIGS. 2 and 3, the surface 9 is shown with a vibration sensor 12 coupled to the surface 9. Various types of vibration sensors can be used to detect the unique vibration signals generated by the medication container with the kinetic augmented attachment. Piezoelectric sensors, which generate an electrical charge in response to mechanical stress, are highly sensitive and reliable for detecting subtle vibrations. Accelerometers, which measure both static and dynamic forces, offer high-resolution vibration monitoring and are commonly used in various applications. Additionally, MEMS (Micro-Electro-Mechanical Systems) vibration sensors, known for their compact size, low cost, and low power consumption, are widely used in consumer electronics for detecting vibrations and movement. Furthermore, geophones, which are typically used for seismic measurements, may be used. Geophones convert ground movement or surface vibrations into voltage signals. They are suitable for detecting low-frequency vibrations generated by objects impacting surfaces. Each of these sensor types can be chosen based on the system's specific requirements, such as sensitivity, frequency range, and operating environment.

Multiple vibration sensors 12 (e.g., 12*a*, 12*b*, 12*c*, etc.) may be used and may be positioned to capture the vibration signals created by interactions with the surface 9. These sensors 12 can be strategically placed on or near the surface where the container 2 is placed, allowing for the detection of unique vibration patterns that reflect the characteristics of the object and the nature of the interaction.

The system 10 may also include an analog-to-digital converter (ADC) 14 coupled to each of the vibration sensors 12. The digitized signals are then transmitted to a computing device 200 (FIG. 4), which performs event detection, kinetic aware time frequency feature extraction, and classification of the detected signals.

The computing device 200 includes at least one processor 202 connected to a central control hub 204. The hub 204 may include components such as a memory controller 220 and an input/output (I/O) controller 222. A memory 206 and a graphics adapter 212 can be connected to the memory controller 220, while a display 218 may be connected to the graphics adapter 212. The system may also include a storage device 208, input devices like a keyboard 210 and a pointing device 214, and a network adapter 216, all of which can be connected to the I/O controller 222. Other configurations of computing device 200 may have different architectures.

The storage device 208 can be a computer-readable medium, such as a hard drive, solid-state drive, compact disk, or DVD, used to store instructions and data for the processor 202. The pointing device 214, which could be a mouse, trackball, or similar, works in combination with the keyboard 210 to facilitate user input. The graphics adapter 212 is responsible for rendering images and outputting them to the display 218. The network adapter 216 connects the computing device 200 to one or more networks for communication with other systems.

The computing device 200 is designed to execute program modules that provide the processing tasks described in this disclosure. These modules can be implemented in hardware, firmware, and/or software. In one embodiment, program modules are stored on the storage device 208, loaded into the memory 206, and executed by the processor 202.

The specific computing systems used herein can vary based on the processing requirements. For example, some systems might include multiple servers working in tandem to perform complex tasks, while others, such as client devices, might be mobile phones or other portable devices with more limited processing power.

Figures 5, 6, 7:
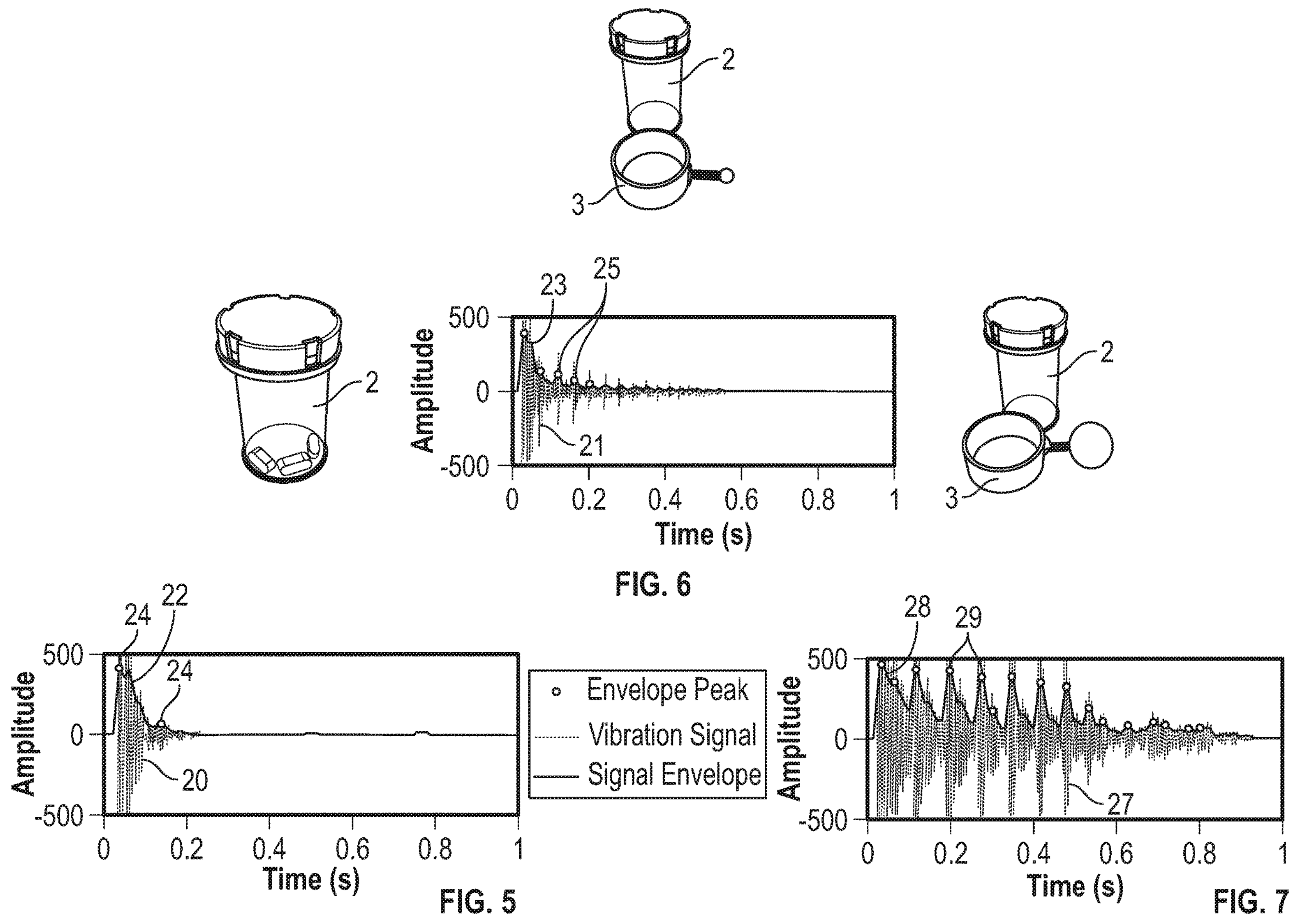
FIG. 5 shows plots of a vibration signal and a corresponding signal envelope for a medication container without a kinetic augmentation attachment according to an embodiment of the present disclosure.
FIG. 6 shows plots of a vibration signal and a corresponding signal envelope for a medication container with a kinetic augmentation attachment according to one embodiment of the present disclosure.
FIG. 7 shows plots of a vibration signal and a corresponding signal envelope for a medication container with a kinetic augmentation attachment according to another embodiment of the present disclosure.

The computing device 200 is configured to receive vibration signals from the vibration sensor 12 and process the data, e.g., perform signal processing. With reference to FIGS. 5-7, the vibration signals may be used to generate vibration signal plots. FIG. 5 shows medication container 2 without the attachment 3 and a corresponding, baseline vibration signal plot 20 that was generated when the medication container 2 was placed on surface 9. A corresponding signal envelope plot 22 is also generated based on the detected envelope peaks 24. The computing device 200 is configured to perform the calculations for identifying the envelope peaks 24 and generating the envelope plot 22.

FIG. 6 shows a medication container 2 with the kinetic augmented attachment 3, which includes a metal ball secured to the base 4 via the spring 5. The corresponding vibration signal plot 21 generated when the medication container 2 was placed on surface 9 is displayed in FIG. 6. A signal envelope plot 23 has also been generated based on the detected envelope peaks 25.

Similarly, FIG. 7 shows a medication container 2 with the kinetic augmented attachment 3, but in this case, the weight 6 is a rubber ball. The corresponding vibration signal plot 27 is shown beneath the setup, along with the signal envelope plot 28 generated based on the detected envelope peaks 29.

A comparison between the vibration signal plots and signal envelope plots shown in FIGS. 5, 6, and 7 highlights the distinct differences between the types of attachments 3 used with the medication container 2, and the corresponding effects on the generated vibration signals. FIG. 5, which shows the container 2 without any attachment 3, generates a relatively simple vibration signal plot 20 and a signal envelope plot 22 with fewer and less pronounced envelope peaks 24. In contrast, FIG. 6, where the kinetic augmented attachment 3 includes a metal ball, the plot displays a more complex vibration signal plot 21 with multiple prominent envelope peaks 25 in the signal envelope plot 23. FIG. 7, featuring a rubber ball as the attachment 3, shows a vibration signal plot 27 with a different pattern of envelope peaks 28 compared to the metal ball in FIG. 6. The signal envelope plot 28 for the rubber ball demonstrates a longer decay time and more closely spaced envelope peaks than those seen in the metal ball configuration.

These differences in the envelope peaks and the overall signal envelope allow the computing device 200 to differentiate between the types of attachments used and, consequently, the specific medication container 2 to which each attachment is coupled. The unique vibration patterns generated by the different materials and configurations of the attachments 3 (e.g., metal vs. rubber) are processed by the computing device 200 to identify and classify the containers, providing a reliable method for distinguishing between various medication containers based on their kinetic augmented attachments.

Figures 8, 9, 10, 11, 13, 14, 15:
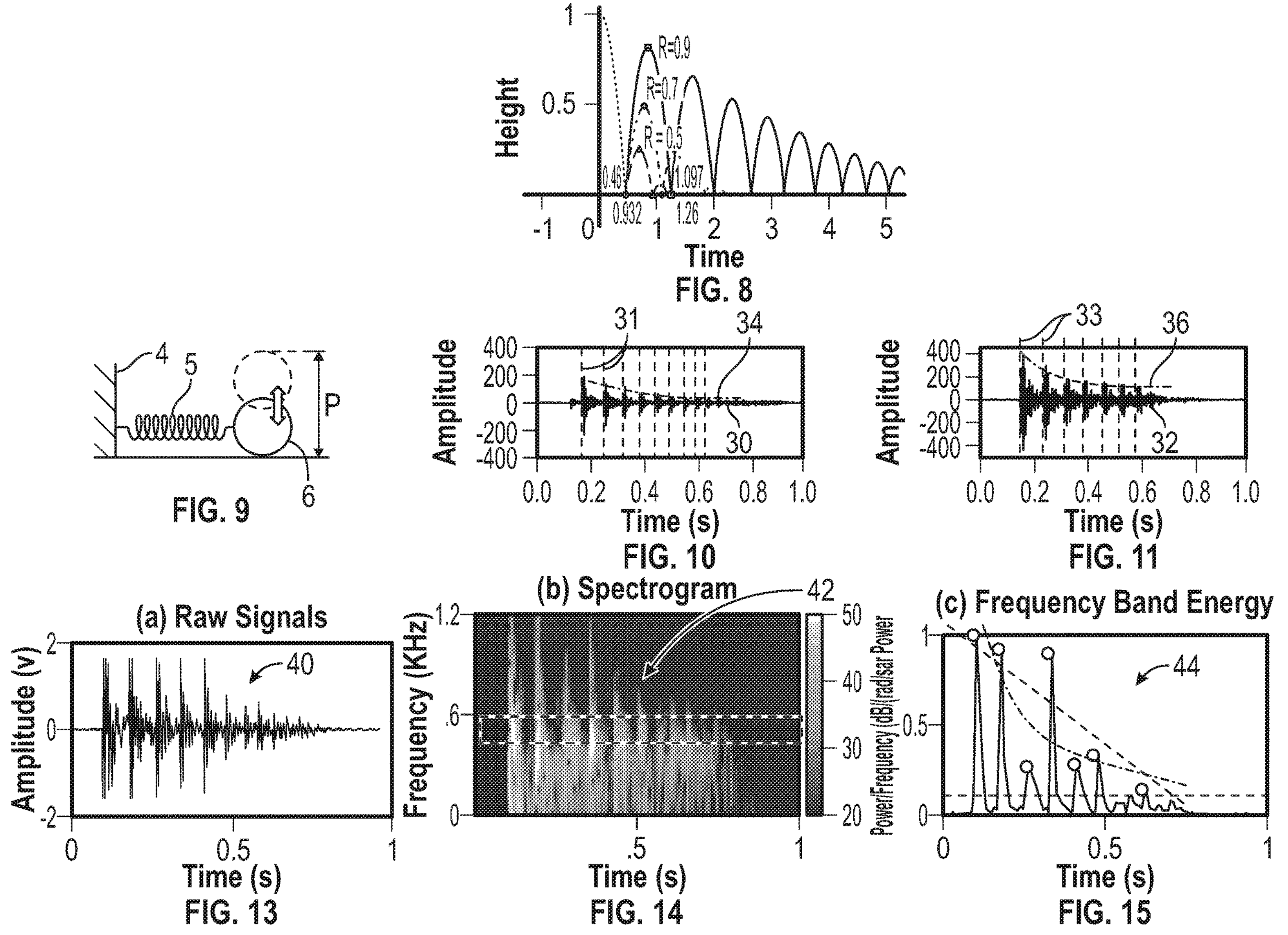
FIG. 8 shows plots of bounce heights as a function of time at different restitutions according to one embodiment of the present disclosure.
FIG. 9 shows a schematic diagram of a model kinetic augmentation attachment according to an embodiment of the present disclosure.
FIG. 10 shows a plot of a vibration signal and a decay plot of the bounces for a medication container of FIG. 6.
FIG. 11 shows a plot of a vibration signal and a decay plot of the bounces for a medication container of FIG. 7.
FIG. 13 is a plot of a vibration signal for a medication container with a kinetic augmentation attachment obtained using the method of FIG. 12 according to one embodiment of the present disclosure.
FIG. 14 is a spectrogram of a portion of the plot of the vibration signal of FIG. 13 obtained using the method of FIG. 12 according to one embodiment of the present disclosure.
FIG. 15 is a frequency band energy diagram of a portion of the spectrogram of FIG. 14 obtained using the method of FIG. 12 according to one embodiment of the present disclosure.

The detected vibration signal generated by the kinetic augmented attachment 3 can be explained through the principles outlined in the ideal bouncing ball model, as shown in FIG. 8. In this model, the height of a bouncing object (e.g., weight 6) over time is influenced by its coefficient of restitution (COR), denoted as R. The COR describes the elasticity of the collision between the object and the surface, which is defined as the ratio of the final velocity to the initial velocity after impact. Different materials and configurations will exhibit varying COR values, resulting in different bounce intervals f and height amplitudes h, as depicted in the plot.

For example, as the COR decreases from $R=0.9$ to $R=0.5$, the height of each subsequent bounce reduces significantly, and the time interval between bounces shortens. These variations in the bouncing pattern are directly related to the material properties of the attachment, such as its elasticity and the stiffness of the spring. The kinetic augmented attachment, with its specific material composition and structural design, generates a distinct vibration signal that can be used for identifying the object.

In the context of the system detecting vibration signals, these principles allow the computing device 200 to analyze the signal generated during the interaction of medication container 2 with the surface 9. By detecting the key features of the signal, such as the time between bounces and the decaying amplitude of the vibration, the system 10 can determine the type of kinetic augmentation attachment 3 attached to the container 2. This unique signature, governed by the restitution properties of the attachment, enables robust identification and differentiation between containers based on the physical attributes of their attachments.

To further verify the feasibility of embedding a unique identification into the object's kinetic signature, a feasibility study was conducted as illustrated in FIG. 9. In this setup, a spring-attached bouncing ball was used. The ball was lifted to a designated height and released, allowing it to freely fall and bounce. The resulting vibrations were captured using a vibration sensor, such as a geophone, placed on the same surface. FIGS. 10 and 11 display the vibration signals as plots 30 and 32 generated when a metal ball (FIG. 10) and a rubber ball (FIG. 11), respectively, were used in the setup.

As shown in FIGS. 10 and 11, the captured vibration signals are represented by the plots 30 and 32, while the dashed lines 31 and 33, respectively, mark each bounce-induced impulsive signal. These impulsive signals are generated when the weight 6 reaches zero height during its bounce cycle. Solid lines 34 and 36 of FIGS. 10 and 11 depict the general decay trend of the bounce signal amplitudes. The distinct differences in the bounce intervals and the decay of the amplitude for the metal ball compared to the rubber ball demonstrate how the kinetic properties of the object can produce unique vibration signatures.

This variation in bounce intervals and signal decay confirms the ability of the system 10 to differentiate between different objects or attachments based on their kinetic signatures. By adjusting the kinetic properties—such as the material, size, and elasticity of the attachment—it is possible to generate a unique vibration profile for each object. These unique profiles, which can be detected and analyzed by the system, allow for the reliable identification and differentiation of various objects, such as different medication containers 2 to which different kinetic augmented attachments 3 are attached. This feasibility study validates the concept of embedding identity into an object's vibration signals, enhancing the system's ability to recognize specific containers based on the kinetic characteristics for each container's respective kinetic augmented attachment.

Figure 12:
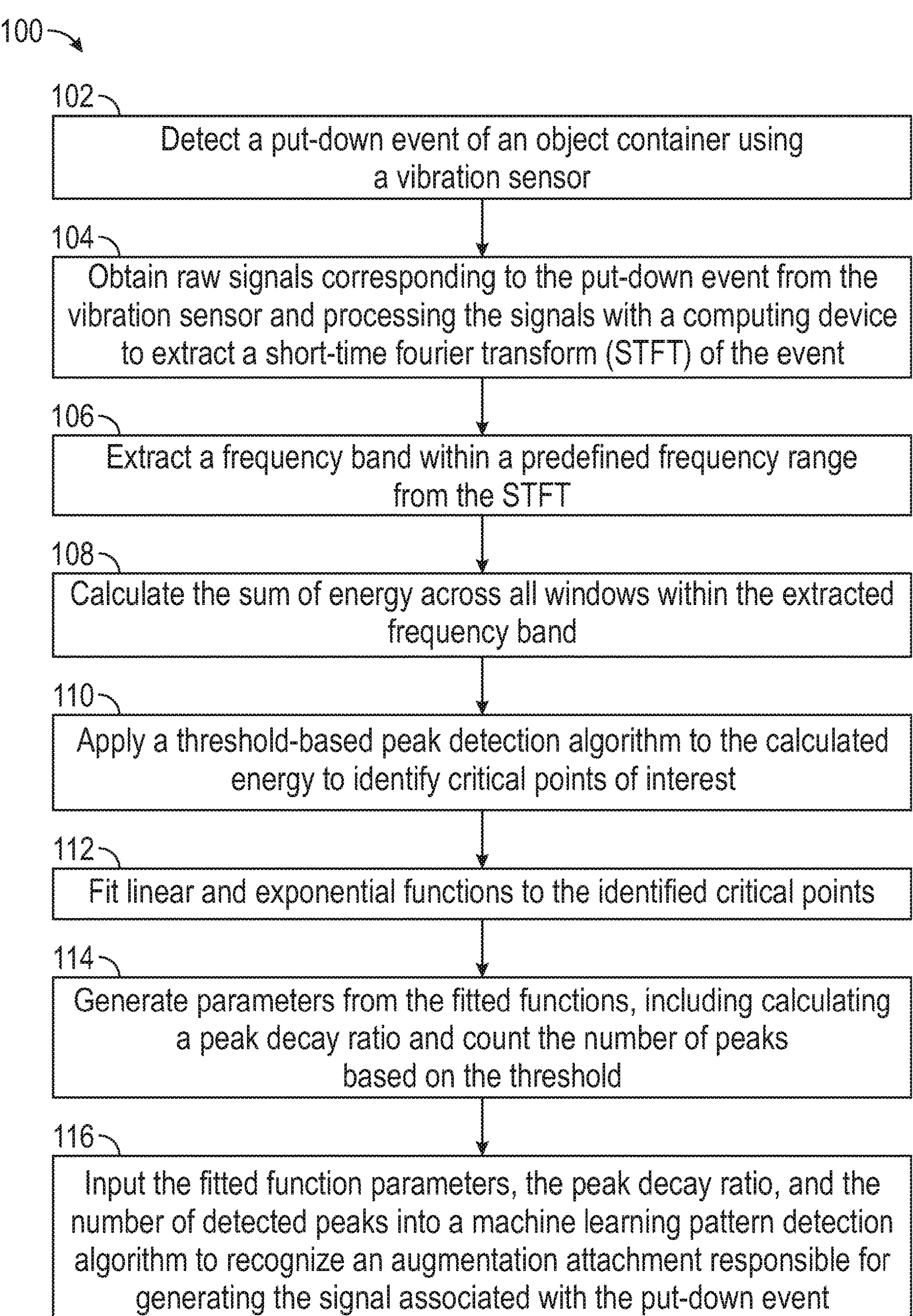
FIG. 12 is a flow chart of a method for identifying a kinetic augmentation attachment based on a vibration signal according to an embodiment of the present disclosure.

A method 100 for detecting and recognizing a put-down event of an object container, as illustrated in FIG. 12, can be described in detail with reference to the steps outlined and the corresponding plots in FIGS. 13, 14, and 15. The method may be embodied as software instructions stored in memory (i.e. memory 206 illustrated in FIG. 4) executable by a processor (i.e. processor 202 illustrated in FIG. 4), thus the method is performed by the computing device 200 and includes multiple steps of signal processing and feature extraction to accurately identify the kinetic augmentation attachment 3 and, consequently, the specific object container 2 associated with the event. The steps of method 100 may be performed in any sequence and the order they are presented in FIG. 12 is exemplary.

The method 100 begins by detecting the put-down event of the medication container 2 using the vibration sensor 12, as shown in FIG. 12, step 102. The vibration sensor 12 captures raw signals corresponding to the put-down event (see FIG. 13, labeled as raw signals 40), which are then processed by the computing device 200 to extract relevant features. The computing device 200 first applies a Short-Time Fourier Transform (STFT) to the raw signals 40, as demonstrated in FIG. 14, where a spectrogram 42 is generated as illustrated in FIG. 14 (step 104 in FIG. 12).

Next, the method involves extracting a frequency band of interest, which may be between 500 and 600 Hz, from the spectrogram 42, as shown in FIG. 14 (step 106). This frequency band is chosen because it contains features of the vibration signal generated by the kinetic augmentation attachment 3. After identifying this band, the method sums the energy within the band across all time windows, generating a plot 44 of the total energy over time (step 108), as depicted in FIG. 15.

Following this, the computing device 200 applies a threshold-based peak detection algorithm to identify critical points of interest in the energy plot 44 (step 110). These points correspond to key moments in the signal, such as the bounce impacts of the kinetic augmentation attachment 3. The detected peaks are then used to fit both linear and exponential functions to the decay of the signal, providing additional insight into the kinetic characteristics of the attachment 3 (step 112).

The method continues by generating parameters from the fitted functions, including the peak decay ratio and the number of detected peaks (step 114). These parameters are then input into a machine learning algorithm, such as a Radial Basis Function (RBF) kernel Support Vector Machine (SVM), to recognize the specific kinetic augmentation attachment 3 responsible for generating the vibration signal (step 116). This allows the system to classify the attachment 3 and thereby identify the associated medication container 2.

The method described provides a comprehensive and efficient approach to recognizing medication containers based on the unique kinetic signatures embedded in the vibration signals. The plots in FIGS. 13, 14, and 15 illustrate the steps of the signal processing, from raw signals 20 to frequency band energy, and ultimately enable accurate identification through feature extraction and machine learning.

A method 120 of FIG. 16 builds upon the signal detection and identification process outlined in FIG. 12, adding steps to match the identified kinetic signature with a specific medication container. This method 120 enables the system 10 to not only recognize the vibration signal but also associate it with the correct container 2, allowing for precise monitoring of medication intake.

A database of known kinetic signatures for various kinetic augmentation attachments 3 is created (step 122). Each signature in the database represents the unique vibration pattern generated by a specific attachment 3 when placed on a surface 9. This step ensures that the system has a reference set of signatures to compare with newly detected signals. The database may be stored in the memory 206 or storage device 208 of computing device 200 (as illustrated in FIG. 4) or any other suitable location or device, e.g., remote server. In addition, each of the attachments 3 is paired with one of the medication containers 2 and the pairing may be provided to the computing device 200, such that the computing device 200 can identify a specific medication container 2 based on the vibration signature of the attachment 3. In one embodiment, the association between the attachment 3 and the medication container 2 may be stored as a table in the memory 206 or storage device 208 of computing device 200 (as illustrated in FIG. 4).

Similar to FIG. 12, the method 120 detects a put-down event of the medication container 2 using a vibration sensor 12 (step 124). The raw signals captured by the sensor are processed in step 126 by the computing device 200 to extract relevant parameters, such as frequency bands and peak decay ratios, as described in the previous method (steps 104, 106) to identify the kinetic augmentation attachment 3 that is associated with the medication container 2.

Once the signal is processed and the kinetic augmentation attachment 3 is identified, the method proceeds to compare the detected signal parameters (e.g., frequency band, peak decay ratio) with the stored signatures in the database (step 128). This comparison involves calculating a similarity score or applying matching criteria to find the closest match between the detected signal and the stored signatures. The system uses machine learning algorithms, such as RBF kernel SVM, to ensure accurate matching (step 116 in FIG. 12).

After the comparison, the system identifies the specific medication container 2 by mapping the detected signal to the closest matching known signature in the database (step 129). This allows the system to accurately track which medication container was used, thus enabling precise monitoring of medication intake.

In embodiments, this method could involve the use of a graphical user interface (GUI) or a mobile application to allow users (e.g., caregivers or patients) to verify the identified medication container 2. The GUI or application may be executed on a mobile or portable version of the computing device 200 and may display information such as the container's medication, the detected signal's match with the database, and potential medication adherence reports. The initial pairing of attachment 3 to the medication container 2 may also be performed using the application. Optionally, the computing device 200 may be configured to periodically update or refine the signature database based on new signals or modifications to medication container usage, ensuring the database is updated.

The methods 100 and 120 may be modified based on human behavior. In response to the need for accounting for human behavior variance, long-term data collection may be conducted with a larger number of users over an extended period. The shared data may be stored in a central database accessible by multiple systems 10 allowing for learning from multiple sources. This approach enables the system 10 to capture inter- and intra-personal behavior variance, such as differences in how users interact with medication containers under varying moods or health conditions. Additionally, the detection methods may also be modified to preserve the kinetic augmentation characteristics while minimizing the impact of human variance thereby ensuring robust system performance despite the variations in individual behavior when placing medication containers 2 down on the surface 9.

To address the challenge of false positive detections, especially in cases where users (e.g., dementia patients) interact with the medication containers 2 without actually taking medication, further structural and data-driven solutions may be implemented. The system 10 and the disclosed methods 100 and 120 may be enhanced to detect changes in the amount of medication in the bottle based on the signal generated during a put-down event. By incorporating multiple vibration sensors 12 that detect subtle changes in weight and distribution within the container 2, the system 10 may differentiate between medication interaction inside the container 2 that indicate actual medication intake and those that do not. This enhancement would greatly reduce the occurrence of false positives.

Additional sensors may also be used to provide for robust recognition with overlapping vibration signals from outside sources. The issue of overlapping vibration signals caused by external activities such as people walking, placing other objects on the surface, or traffic outside, etc., may be addressed by separating and extracting container-induced vibration signals in the presence of such noise. By utilizing a pre-built template of the attachment 3 and applying advanced signal processing techniques, the system 10 may isolate and recognize container vibrations from other ambient vibrations. This improvement ensures that the system 10 remains accurate and reliable in environments with a high level of external noise.

EXAMPLES

Example 1

Although illustrated with examples, these examples are not intended to be limiting. The examples describe use of the system 10 to identify different types of medication containers based on their vibration signal signature.

With reference to FIGS. 2, 17, and 18, use of the system 10 and method 100 was demonstrated, with the goal of verifying the robustness and accuracy of medication container recognition based on the vibration signals generated by the kinetic augmentation attachment 3.

As depicted in FIG. 2, the system 10 was tested by placing the augmented medication containers on five distinct locations on the surface 9 measuring 120 cm by 60 cm. These locations were labeled as top-left (T-L), top-right (T-R), middle (M), bottom-left (B-L), and bottom-right (B-R). A vibration sensor 12 was vertically installed in the top-left corner of the surface 9 to capture the put-down events of the medication containers. With reference to FIG. 16, five different medical containers (b)-(f) were used, three of which were unaugmented and two of which were augmented with attachments 3, namely, (e) and (f). Each medical container was put down 50 times at each of the five locations, and the data was recorded for all configurations of the attachment (metal ball, rubber ball, and no augmentation), as illustrated in FIG. 16.

The collected data was analyzed using a Leave-One-Out (LOO) cross-validation method. In this approach, data from one location was selected as the test set, while the remaining four locations were used as training data to ensure the model's robustness against location variance. This method allowed the system to evaluate how well it could recognize the pill bottles despite variations in where they were placed on the table.

Detectability of the system 10 was compared using three medication containers without kinetic augmentation (No KAA) and without kinetic-aware feature and another without the kinetic-aware feature extraction (No KAFE). The accuracy of pill bottle recognition was taken as the primary evaluation metric.

The results are shown as bar graphs in FIG. 17 and demonstrate the recognition accuracy of the kinetically augmented containers (with KAA and KAFE) in comparison to the two baseline methods at each testing location. The kinetically augmented containers achieved near-perfect accuracy at most locations, with 100% accuracy at the top-left, top-right, middle, and bottom-right locations, and 95% accuracy at the bottom-left location. Furthermore, kinetically augmented containers demonstrated robustness against location variance in the LOO test, achieving an average recognition accuracy of 79% across four locations, outperforming both baseline models.

The bottom-left location (B-L) showed a slightly lower accuracy, which might be attributed to structural abnormalities or other environmental factors affecting the consistency of the vibration signals. This Example validates the effectiveness of the kinetic augmentation attachment 3 and the detection system for medication container recognition. The method demonstrates a significant improvement in accuracy over non-augmented systems and highlights the robustness of the kinetically augmented container detection system in varying environmental conditions. The success of this method is essential for enabling precise and non-intrusive monitoring of medication intake in real-world settings.

Alternate embodiments may be devised without departing from the spirit or the scope of the present technology. Additionally, well-known elements of embodiments of the systems, apparatuses, and methods have not been described in detail or have been omitted so as not to obscure the relevant details of the systems, apparatuses, and methods.

The terminology used herein is for the purpose of describing particular embodiments only and is not intended to be limiting. The terms "comprises," "comprising," or any other variation thereof are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element. The terms "including" and/or "having," as used herein, are defined as comprising (i.e., open language). The terms "a" or "an", as used herein, are defined as one or more than one. The term "plurality," as used herein, is defined as two or more than two. The term "another," as used herein, is defined as at least a second or more. The description may use the terms "embodiment" or "embodiments," which may each refer to one or more of the same or different embodiments.

When the terms "coupled" and "connected," along with their derivatives, are used, these terms are not intended as synonyms for each other. For example, "connected" may be used to indicate that two or more elements are in direct physical or electrical contact with each other. "Coupled" may mean that two or more elements are in direct physical or electrical contact (e.g., directly coupled) or that two or more elements are not in direct contact with each other but yet still cooperate or interact with each other (e.g., indirectly coupled).

For the purposes of the description, a phrase in the form "A/B" or in the form "A and/or B" or in the form "at least one of A and B" means (A), (B), or (A and B), where A and B are variables indicating a particular object or attribute. When used, this phrase is intended to and is hereby defined as a choice of A or B or both A and B, which is similar to the phrase "and/or". Where more than two variables are present in such a phrase, this phrase is hereby defined as including only one of the variables, any one of the variables, any combination of any of the variables, and all of the variables, for example, a phrase in the form "at least one of A, B, and C" means (A), (B), (C), (A and B), (A and C), (B and C), or (A, B and C).

Relational terms such as first and second, top and bottom, and the like may be used solely to distinguish one entity or action from another entity or action without necessarily requiring or implying any actual such relationship or order between such entities or actions. The description may use perspective-based descriptions such as up/down, back/front, top/bottom, and proximal/distal. Such descriptions are merely used to facilitate the discussion and are not intended to restrict the application of disclosed embodiments. Various operations may be described as multiple discrete operations in turn, in a manner that may be helpful in understanding embodiments; however, the order of description should not be construed to imply that these operations are order dependent.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. As used herein, the terms "substantial" and "substantially" means, when comparing various parts to one another, that the parts being compared are equal to or are so close enough in dimension that one skill in the art would consider the same. Substantial and substantially, as used herein, are not limited to a single dimension and specifically include a range of values for those parts being compared. The range of values, both above and below (e.g., "+/−" or greater/lesser or larger/smaller), includes a variance that one skilled in the art would know to be a reasonable tolerance for the parts mentioned.

Various embodiments of the systems, apparatuses, and methods have been described, and in many of the different embodiments many features are similar. To avoid redundancy, repetitive description of these similar features may not be made in some circumstances. It shall be understood, however, that description of a first-appearing feature applies to the later described similar feature and each respective description, therefore, is to be incorporated therein without such repetition.

From the foregoing, it will be appreciated that specific embodiments of the disclosure have been described herein for purposes of illustration, but that various modifications may be made without deviating from the scope of the disclosure. Accordingly, the disclosure is not limited except as by the appended claims. The following Examples illustrate embodiments of the present disclosure. These Examples are intended to be illustrative only and are not intended to limit the scope of the present disclosure. Also, parts and percentages are by weight unless otherwise indicated.

What is claimed is:

1. A system for monitoring medication intake based on interaction with a medication container, the system comprising:

a kinetic augmentation attachment configured to be coupled to the medication container, the attachment including:

a base for coupling to the medication container;

a spring coupled to the base at a first end; and a weight coupled to a second end of the spring, wherein the kinetic augmentation attachment generates a vibration signal when the medication container is placed on a surface;

at least one vibration sensor configured to detect the vibration signal generated by the placement of the medication container on the surface; and a computing device in communication with the vibration sensor, the computing device configured to:

receive the vibration signal from the vibration sensor;

process the vibration signal to extract features indicative of the kinetic augmentation attachment; and identify the medication container coupled to the kinetic augmentation attachment based on the extracted features.

2. The system of claim 1, wherein the weight is formed from one of metal, rubber, or thermoplastic polymer.

3. The system of claim 1, wherein the spring is one of a coil spring, an elastomeric rod, or a leaf spring.

4. The system of claim 1, wherein the computing device is further configured to apply a Short-Time Fourier Transform (STFT) to the received vibration signal to generate a spectrogram for analysis.

5. The system of claim 4, wherein the computing device is further configured to:

extract a frequency band from the spectrogram;

sum energy across the extracted frequency band; and use a peak detection algorithm to identify points of interest in the signal.

6. The system of claim 1, wherein the computing device is further configured to access a database storing kinetic signatures corresponding to a plurality of kinetic augmentation attachments and a medication container corresponding to at least one kinetic augmentation attachment of the plurality of kinetic augmentation attachments.

7. The system of claim 6, wherein the computing device is further configured to compare the extracted features of the detected vibration signal to the stored kinetic signatures in the database to match the vibration signal with a specific medication container.

8. The system of claim 1, wherein the computing device is further configured to execute a machine learning algorithm to identify the kinetic augmentation attachment based on the extracted features.

9. The system of claim 8, wherein the machine learning algorithm is a support vector machine.

10. The system of claim 1, wherein the vibration sensor is a piezoelectric sensor, an accelerometer, or a MEMS vibration sensor.

11. A method for identifying a medication container, the method comprising:

detecting a vibration signal using a vibration sensor, the vibration signal generated by placing a medication container on a surface, the medication container having a kinetic augmentation attachment including:

a base for coupling to the medication container;

a spring coupled to the base at a first end; and a weight coupled to a second end of the spring, wherein the kinetic augmentation attachment generates a vibration signal when the medication container is placed on a surface;

processing the vibration signal to extract signal features indicative of the kinetic augmentation attachment;

identifying the medication container coupled to the kinetic augmentation attachment based on the detected vibration signal; and outputting the identified medication container to a user.

12. The method of claim 11, wherein the weight is formed from metal, rubber, or thermoplastic polymer.

13. The method of claim 11, wherein the spring is a coil spring, an elastomeric rod, or a leaf spring.

14. The method of claim 11, further comprising:

applying a Short-Time Fourier Transform (STFT) to the vibration signal to generate a spectrogram for analysis.

15. The method of claim 14, further comprising:

extracting a frequency band from the spectrogram;

summing energy across the extracted frequency band; and identifying points of interest in the signal using a peak detection algorithm.

16. The method of claim 11, further comprising:

accessing a database storing kinetic signatures corresponding to a plurality of medication containers and corresponding kinetic augmentation attachments.

17. The method of claim 16, further comprising:

comparing the extracted signal features of the detected vibration signal to the stored kinetic signatures in the database to match the vibration signal with a specific medication container.

18. The method of claim 11, further comprising:

using a machine learning algorithm to identify the kinetic augmentation attachment based on the extracted signal features.

19. The method of claim 18, wherein the machine learning algorithm is a support vector machine.

20. The method of claim 11, wherein the vibration sensor is one of piezoelectric sensors, accelerometers, or MEMS vibration sensors.

* * * * *